(12) United States Patent
Siccardi et al.

(10) Patent No.: US 9,138,333 B2
(45) Date of Patent: Sep. 22, 2015

(54) INTERVERTEBRAL IMPLANT FOR THE FUSION BETWEEN TWO VERTEBRAL BODIES OF A VERTEBRAL COLUMN AND CORRESPONDING POSITIONING INSTRUMENT

(75) Inventors: Francesco Siccardi, Vico Morcote (CH); Meinrad Fiechter, Lugano (CH); Dezsö Jeszenszky, Küsnacht (CH); Zsolt Fekete, Bremen (DE); Christoph E. Heyde, Leipzig (DE)

(73) Assignee: MEDACTA INTERNATIONAL SA, Casel San Pietro (CH)

( * ) Notice: Subject to any disclaimer, the term of this patent is extended or adjusted under 35 U.S.C. 154(b) by 23 days.

(21) Appl. No.: 13/457,942

(22) Filed: Apr. 27, 2012

(65) Prior Publication Data

US 2012/0277869 A1  Nov. 1, 2012

(30) Foreign Application Priority Data

Apr. 29, 2011  (EP) ..................... 11164253

(51) Int. Cl.
*A61F 2/44* (2006.01)
*A61F 2/46* (2006.01)
(Continued)

(52) U.S. Cl.
CPC ............. *A61F 2/4611* (2013.01); *A61F 2/4465* (2013.01); *A61F 2002/2835* (2013.01); *A61F 2002/302* (2013.01); *A61F 2002/30112* (2013.01); *A61F 2002/30133* (2013.01); *A61F 2002/30538* (2013.01); *A61F 2002/30594* (2013.01); *A61F 2002/30777* (2013.01); *A61F 2002/30779* (2013.01); *A61F 2002/30841* (2013.01); *A61F 2002/4622* (2013.01); *A61F 2230/0004* (2013.01); *A61F 2230/0015* (2013.01); *A61F 2230/0065* (2013.01); *A61F 2250/0006* (2013.01); *A61F 2250/0098* (2013.01)

(58) Field of Classification Search
CPC ......... A61F 2/44; A61F 2/442; A61F 2/4455; A61F 2/446; A61F 2/4465; A61F 2/447; A61F 2/46; A61F 2/4603; A61F 2/4611; A61F 2002/443; A61F 2002/4475; A61F 2002/4622; A61F 2002/4625; A61F 2002/4628; A61F 2002/4629; A61F 2002/4635; A61B 17/88; A61B 17/8872; A61B 2017/0256
USPC ............... 623/17.11–17.16; 606/99, 100, 914
See application file for complete search history.

(56) References Cited

U.S. PATENT DOCUMENTS 6,159,215 A   12/2000 Urbahns et al.
6,319,257 B1  11/2001 Carignan et al.
(Continued)

FOREIGN PATENT DOCUMENTS

EP   1841385 B1    3/2010
WO   2008036636 A2  3/2008
WO   2008146983 A1  12/2008

*Primary Examiner* — Kevin T Truong
*Assistant Examiner* — Tracy Kamikawa
(74) *Attorney, Agent, or Firm* — Allen, Dyer, Doppelt, Milbrath & Gilchrist, P.A.

(57) ABSTRACT

An intervertebral implant for the fusion between two vertebral bodies of a vertebral column may include a body having two opposite surfaces and holes or cavities for filling purposes during bone growth, and an engagement portion for receiving a gripping end of a positioning instrument. The engagement portion may be shaped as a splined shaft accessible through an opening of the body.

16 Claims, 11 Drawing Sheets

(51) Int. Cl.
*A61F 2/28* (2006.01)
*A61F 2/30* (2006.01)

(56) References Cited

U.S. PATENT DOCUMENTS

| | | | |
|---|---|---|---|
| 6,923,814 | B1 | 8/2005 | Hildebrand et al. |
| 6,974,480 | B2 * | 12/2005 | Messerli et al. ........... 623/17.16 |
| 2004/0153065 | A1 | 8/2004 | Lim |
| 2005/0096745 | A1 | 5/2005 | Andre et al. |
| 2006/0229627 | A1 | 10/2006 | Hunt et al. |
| 2006/0235426 | A1 | 10/2006 | Lim et al. |
| 2007/0093897 | A1 * | 4/2007 | Gerbec et al. .............. 623/17.11 |
| 2007/0213737 | A1 * | 9/2007 | Schermerhorn et al. ........ 606/86 |
| 2007/0225808 | A1 | 9/2007 | Warnick |
| 2008/0065082 | A1 | 3/2008 | Chang et al. |
| 2008/0082173 | A1 * | 4/2008 | Delurio et al. ............. 623/17.16 |
| 2008/0262623 | A1 * | 10/2008 | Bagga et al. ............. 623/17.16 |
| 2010/0191337 | A1 * | 7/2010 | Zamani et al. ............. 623/17.16 |

* cited by examiner

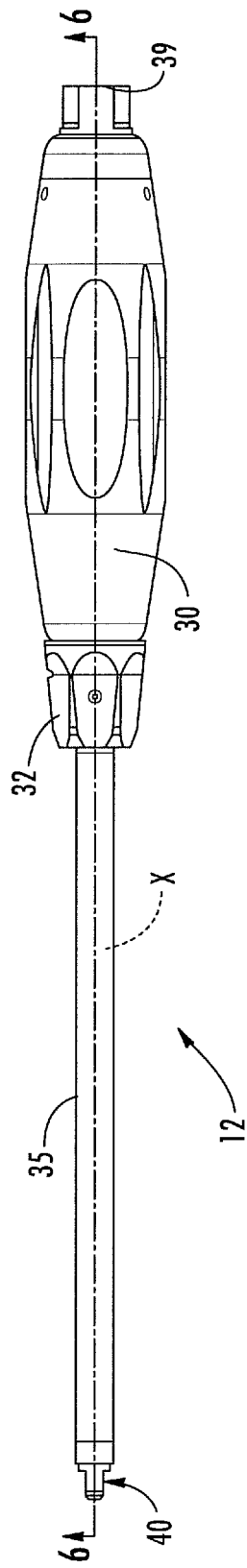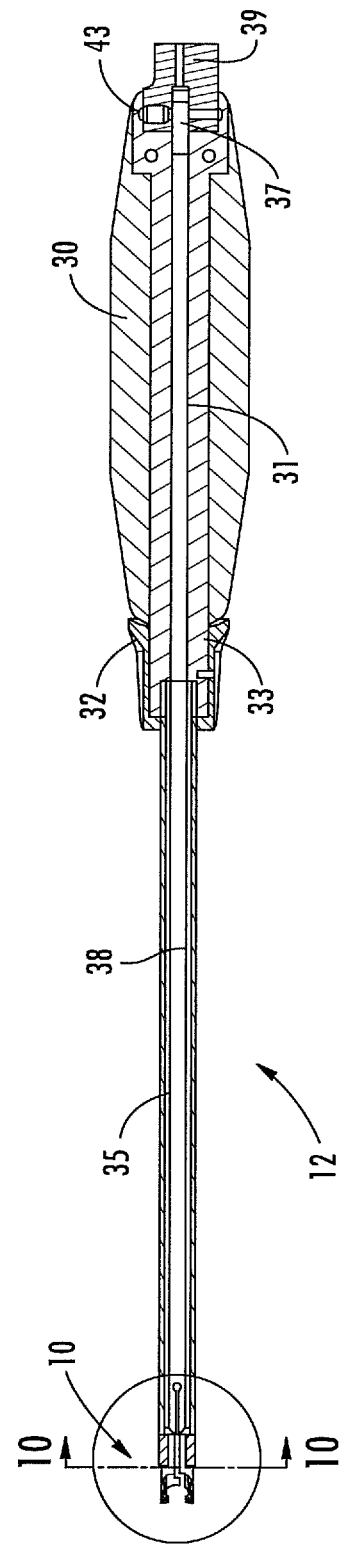
FIG. 5
FIG. 6

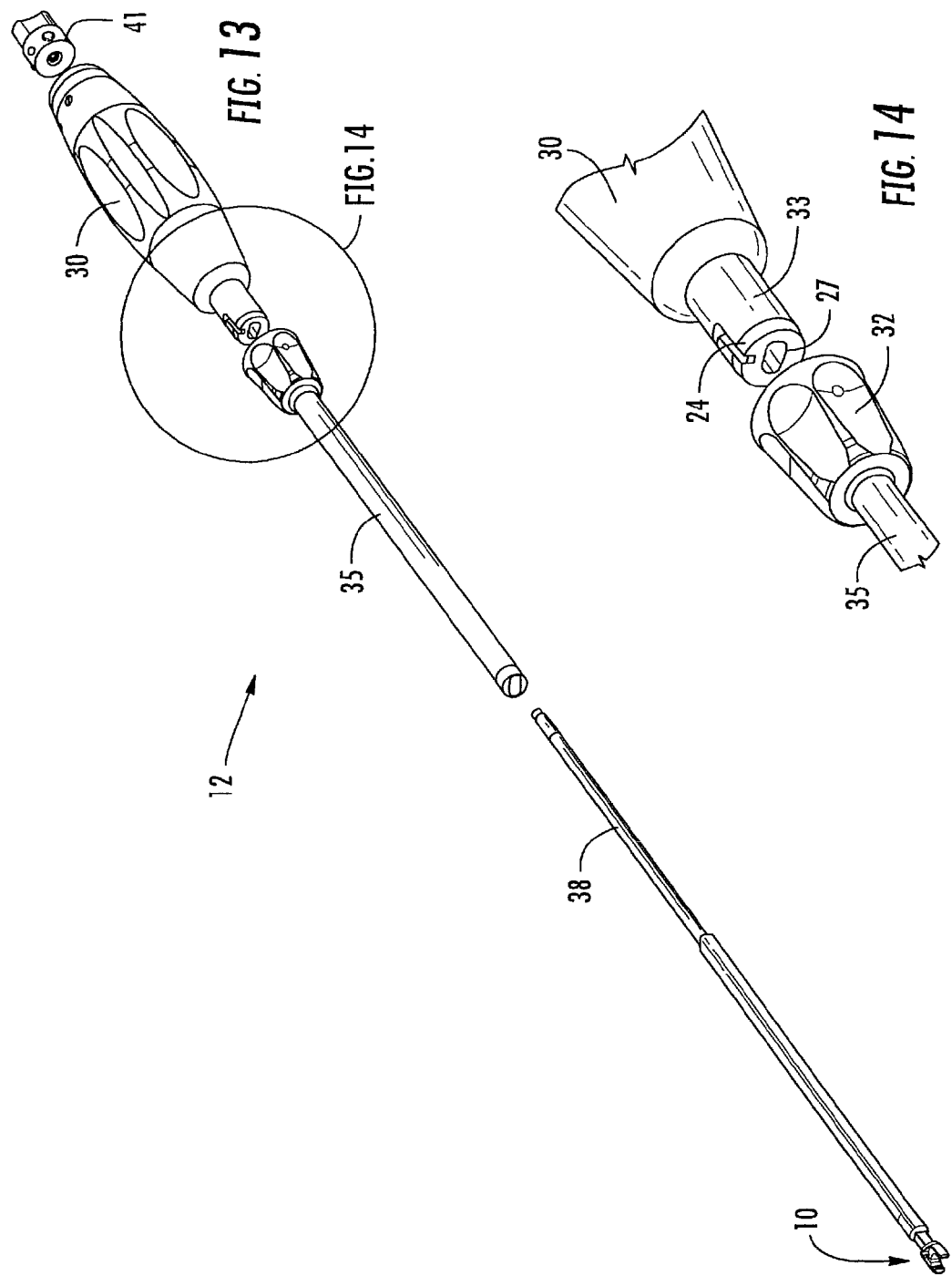

INTERVERTEBRAL IMPLANT FOR THE FUSION BETWEEN TWO VERTEBRAL BODIES OF A VERTEBRAL COLUMN AND CORRESPONDING POSITIONING INSTRUMENT

FIELD OF THE INVENTION

The present invention relates to an intervertebral implant for fusion between vertebral bodies of a vertebral column, and in particular, to an implant for the Transforaminal Interbody Fusion (TLIF) of lumbar vertebral column segments.

BACKGROUND OF THE INVENTION

As is known in this technical field, various attempts have been made to use minimally invasive surgery for spine operations. In this respect, so-called PLIF (Posterior Lateral Interbody Fusion) operation techniques have been developed. According to such an operation technique, the intervertebral disc is removed through a posterior access and an intervertebral space is filled with autologous bone.

Further developments of this PLIF technique resulted in the application of a so-called TLIF operation technique based on a transforaminal access. This technique provides for the dorsal transforaminal introduction of titanium cups (so-called cages), which are filled with autologous bone. At the same time, dorsal instrumentation and stabilization are applied.

The advantage of the briefly outlined method is that no transabdominal or retroperitoneal additional access has to be used. A known prior art approach is described in the U.S. Pat. No. 6,923,814, which discloses a system for performing spinal fusion between adjacent cervical vertebrae, including an implant and an introduction system. The introduction system comprises a fork member and a general tubular lock member. A thread feature at the end of the instruments transfers a rotational movement into a linear movement. The linear movement causes the deformation of the fork member and therefore engagement of the instrument with the implant. The implant instrument locking is done by a thread member that, however, does not simplify the working steps compared to a simple thread. In case of a 90° locking, less manipulation steps may be required, but the instrument does not allow angularly adjustment of the implant with respect to the instrument.

Another approach is disclosed in the U.S. Pat. No. 6,159,215, disclosing a method for delivering a vertebral body spacer to the disc space. The instrument has two fingers, which are movable relative to one another and adapted to grip the spacer when the shaft is moved to actuate the fingers. The handle portion includes a grip and a trigger for the grip, causing the fingers to move toward one another. The implant is not, in-situ, angularly adjustable. The fixation is done by way of a linear movement.

Another approach is described in the U.S. Patent Application Publication No. 2006/0235426, which discloses an implant, and an instrument and method for positioning a spinal implant in a spinal disc space between adjacent vertebrae. That implant is fixed by a hinged forceps tip. The forceps tip can be angularly adjusted with respect to the implant and the instrument is permanently connected to the implant. This approach has a complex instrument locking mechanism instead of a 90° lock/unlock mechanism and it's impossible to engage the instrument in-situ.

Another approach is disclosed in the U.S. Pat. No. 66,174, which discloses an implant insertion device with a gripping device on one end. The jaws are movable between the gripping position to grasp the implant between the gripping elements and releasing position to release the implant. A hollow sleeve is slidably disposed over the jaws for forcing the jaws together towards the gripping position. The implant fixation is done with a linear movement of the sleeve, but this linear movement can cause tissue damage and it is not as simple as a 90° locking.

Another approach is disclosed in U.S. Patent Application Publication No. 2004/0153065. The approach includes an intervertebral implant. The instrument is connected to the implant by a hinge element. The rotation of the axial sleeve of the instrument case an axial movement of the shaft. This movement is pivoting the spacer. It is impossible to engage the instrument is-situ. Angulation is mainly possible in only one direction. The engagement/disengagement mechanism may be inferior compared to a 90° locking mechanism because of its complexity.

U.S. Patent Application Publication No. 2005/0096745 discloses an implant for the transforaminal intercorporal fusion of lumbar vertebral column segments. The attachment part to the instrument is configured as a slot. Within this slot, the instrument can be engaged. The instrument can be fixed in different angles with respect to the implant. The interface is a friction lock, which has reduced stability compared to a positive lock. The fixation is done by a thread mechanism. The engagement/disengagement mechanism may be less desirable as compared to a 90° locking mechanism because of the required working steps.

Another approach is disclosed in the European Patent No. EP1841385B1. This approach includes an implant for the transforaminal intercorporal fusion of lumbar vertebral column segments. The attachment part to the instrument is configured as a revolute joint. Within the revolute joint, there is a thread as an interface to the instrument. The instrument can be fixed in different angles in respect to the implant. The interface is a friction lock, which has reduced stability as compared to a positive lock. In addition, in-situ engagement is not possible due to the thread. The fixation of the implant to the instrument is more difficult compared to a 90° locking instrument.

SUMMARY OF THE INVENTION

Based on the foregoing, it is an object of the invention to provide an implant for the Transforaminal Intervertebral Fusion of lumbar vertebral column segments.

An object is to provide an implant with high primary stability and that allows a simple operative procedure in use.

An object is to provide an implant with a simple structure and low cost.

An implant for the fusion between two vertebral bodies of a vertebral column may include an engagement portion for receiving a gripping end of a positioning instrument. This may allow a very strong and stable gripping of such a gripping end thanks to a particular shape of the engagement portion.

An approach to the above technical problem may include an intervertebral implant for the fusion between two vertebral bodies of a vertebral column comprising: a body having two opposite surfaces and including holes or cavities for filling purposes during bone growth, and an engagement portion for receiving a gripping end of a positioning instrument. The engagement portion may be shaped as a splined shaft accessible through an opening of the body.

The implant body and the splined shaft are manufactured by a biocompatible radiolucent synthetic material as a single piece construction, for example, by an injection molding. As an alternative, the splined shaft may be realized by a biocompatible metal or metal alloy and is merged inside a biocompatible radiolucent synthetic material forming the implant body. This may allow a stronger engagement of the gripping end with the engagement portion.

Advantageously, the splined shaft may be embedded in the body between the opposite surfaces. More particularly, the splined shaft may be embedded in the body with an axis substantially perpendicular to the opposite surfaces.

Moreover, the splined shaft may have a plurality of peripheral ribs regularly angularly spaced as in a gear. More particularly, the splined shaft may have a plurality of ribs regularly alternated by groves with a regular and relatively small pitch, thus forming the gear shape of the shaft. This particular shape allows the embedded portion to be strongly gripped by the implant body so that there is a strong mechanical integration and fixation between the implant body and the splined shaft if they are made with different materials.

It should be noted that the opening allowing access to the splined shaft may be delimited by at least a lateral wall representing a lateral stop for the possible angular orientation of the gripping end of the positioning instrument. The splined shaft may be accessible through the opening for about 270° of its lateral periphery.

The implant body may have a so-called insertion nose at one end, and the splined shaft is accessible at the end opposite to the insertion nose. Due to the presence of the splined shaft close to one end of the implant body, markers may be embedded in the implant body adjacent to the insertion nose end. The opposite surfaces may present a slightly dome shape.

Another aspect is directed to a positioning instrument for an implant including a handle having a proximal and a distal end, a locking shaft extended from the distal end of the handle, and a grasping head at the distal end of the shaft. The locking shaft may be cannulated and a stem is hosted inside the cannulated shaft passing through the handle. The shaft may be rotatable over the stem. The grasping head may be formed at the distal end of the stem with a couple of clamps closing and opening according to an angular rotation of the stem. Advantageously, the cannulated locking shaft has an internal oval section.

Further features and advantages of the implant and the positioning instrument of the present invention will appear from the following description given by way of non limiting example with reference to the enclosed drawings figures.

BRIEF DESCRIPTION OF THE DRAWINGS

FIG. 5 is a side view of a positioning instrument that may be used for implanting the implant of FIG. 1.

FIG. 6 is a cross-sectional view of the instrument of FIG. 5 taken along the line B-B.

FIG. 13 is a perspective view of separate parts of the instrument of FIGS. 5 and 7.

FIG. 14 is a perspective view of a particular of FIG. 13.

DETAILED DESCRIPTION OF THE PREFERRED EMBODIMENTS

With reference to the figures, an intervertebral implant realized according to the present invention permits the fusion between two vertebral bodies of a vertebral column. The implant 1 is specifically intended to be used as an intervertebral body fusion device. The implant 1 has been specifically realized for allowing vertebral operations according to the requirement of the modern Minimally Invasive Surgery. The implant 1 is mainly dedicated to the use in TLIF (Transforaminal Lumbar Intervertebral Fusion) surgery, however, nothing prevents that it may be adopted in other surgery techniques, such as PLIF or OILF.

The implant 1 has a main body 2 realized with a biocompatible radiolucent synthetic material, for example, a Polyetheretherketone (PEEK) structure having a favorable modulus of elasticity. However, other appropriate implant materials are usable as well, for example, with or without a titanium coating.

The body 2 is Kidney-bead shaped and available in several different heights, widths, and lengths. Since this synthetic material is transparent to X-ray, some markers 18 are incorporated in the biocompatible synthetic material of the implant body 2 to allow the surgeon to identify the implant when installed. For example, so-called posterior and anterior markers pins 28 are merged inside the structure of the body 2 to allow a clear and easy visualization of the implant.

Figure 1:
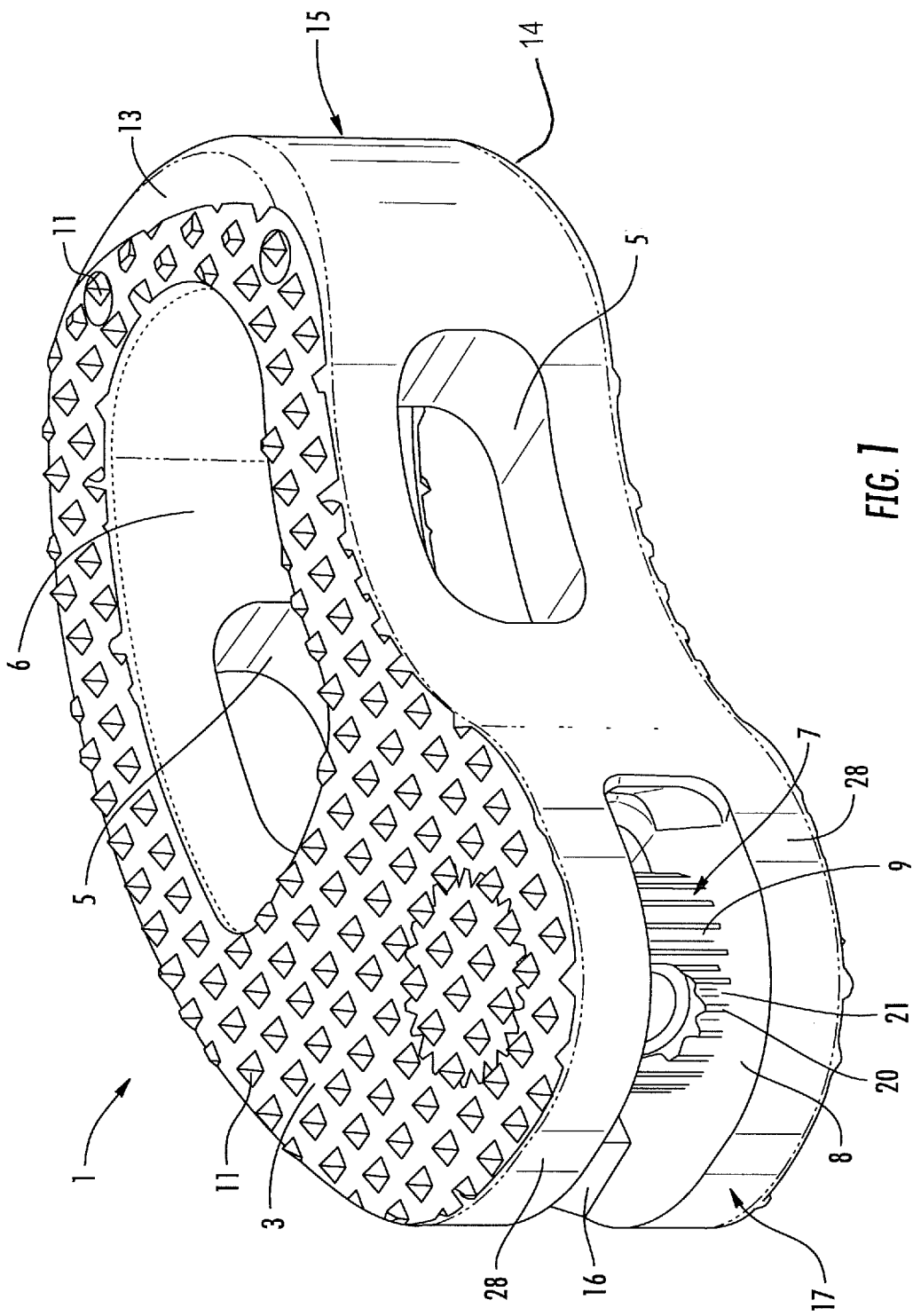
FIG. 1 is a perspective view of an implant for the fusion between two vertebral bodies of a vertebral column, according to the present invention.
Figure 3:
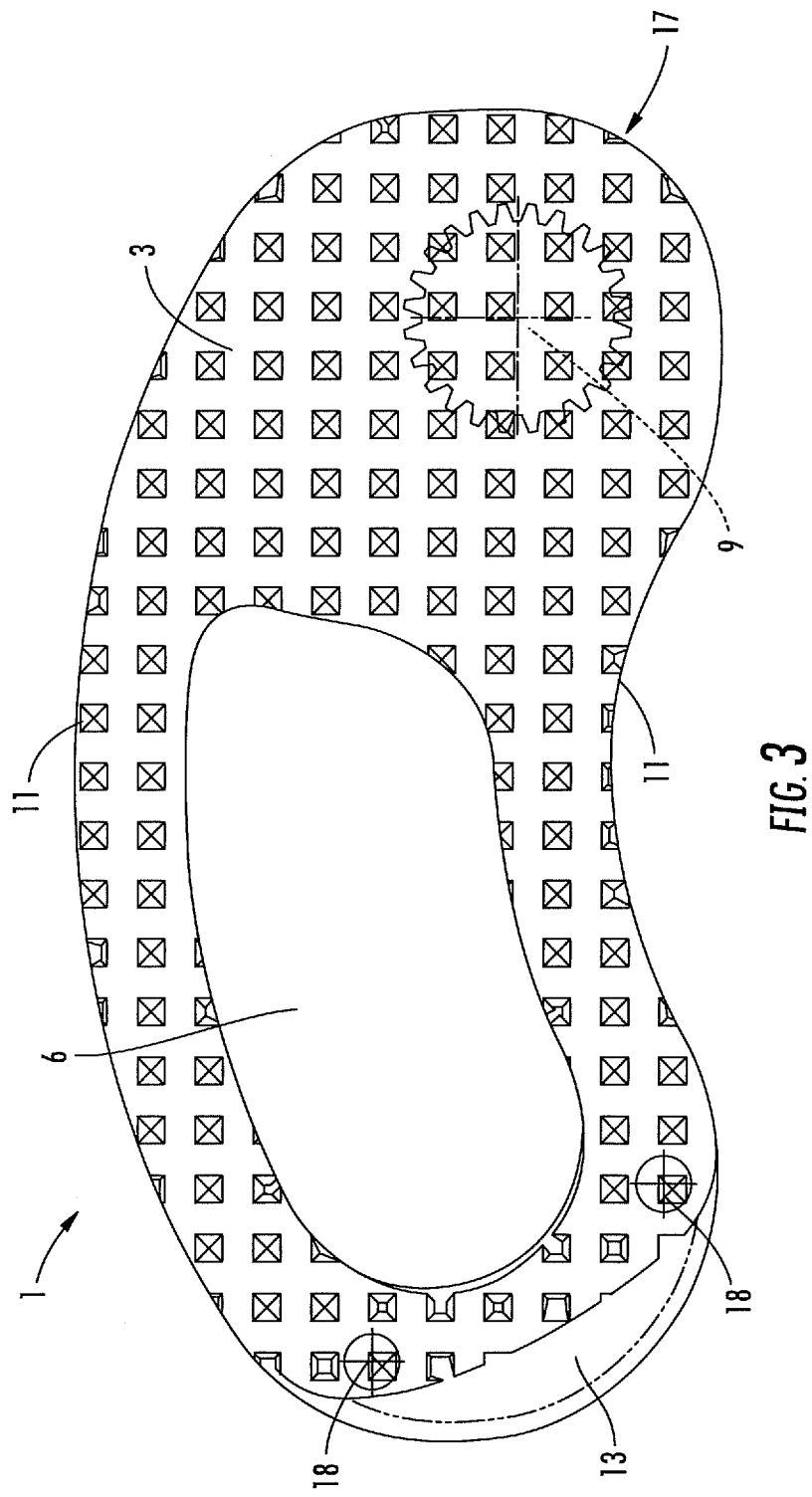

Examples of these X-ray markers are shown in FIGS. 1 and 3 with the numerals 18 and 28. However, these markers 18, 28 may be in larger number and they may be oriented according to the main axis of the implant body 2 or transversely to such an axis. They may be parallel to one another or having converging of overlapping axes.

The body 2 has two opposite surfaces 3 and 4 coming into direct contact with the vertebral column in order to fit the anatomy of the vertebral end plates. The body 2 includes holes 5 or cavities 6 for filling purposes allowing the bone growth (e.g. autogenic bone graft). For example, the holes 5 are provided for the AP bone growth while the cavity 6 is provided for the Caudal-Cranial bone growth.

Each of the surfaces 3 and 4 is slightly dome shaped. Each of the surfaces 3, 4 includes a plurality of teeth 11 in order to provide primal stability and for improving the gripping or adhesion of these surfaces 3, 4 against the corresponding abutting surfaces of the vertebral end plates when the implant 1 is implanted. Those teeth 11 are regularly distributed on each of the surfaces 3 and 4.

Figure 2:
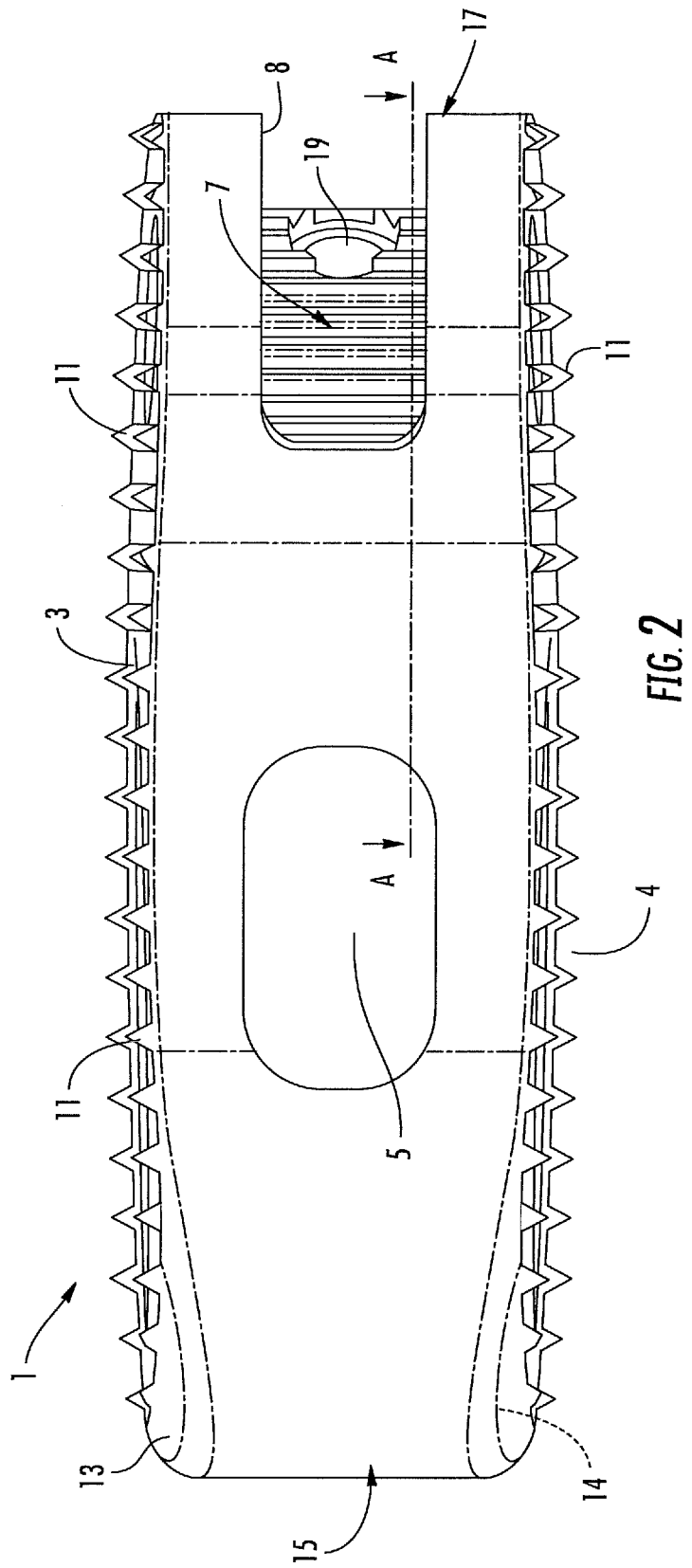
FIGS. 2 and 3 are side and top plan views of the implant of FIG. 1, respectively.

As a whole, the body 2 has a slightly curved shape with opposite ends having rounded edges, as shown in the top view of FIG. 2. One end 15 is named an insertion nose and the surfaces 3 and 4 of the body 2 present tapered portions 13 and 14 in correspondence with the end 15, which serve as an insertion aid providing a self-distracting feature and facilitates the insertion.

Advantageously, according to the illustrated embodiment, an engagement portion 7 is provided in the body 2 for receiving a grasping (grasping, grabbing, etc.) end 10 of a positioning instrument 12. The engagement portion 7 is a splined shaft 9 similar to a gear and that is accessible through a lateral opening 8 of the body 2. This splined shaft 9 has an axis that is substantially perpendicular to the plane of the surfaces 3 and 4.

Figure 4:
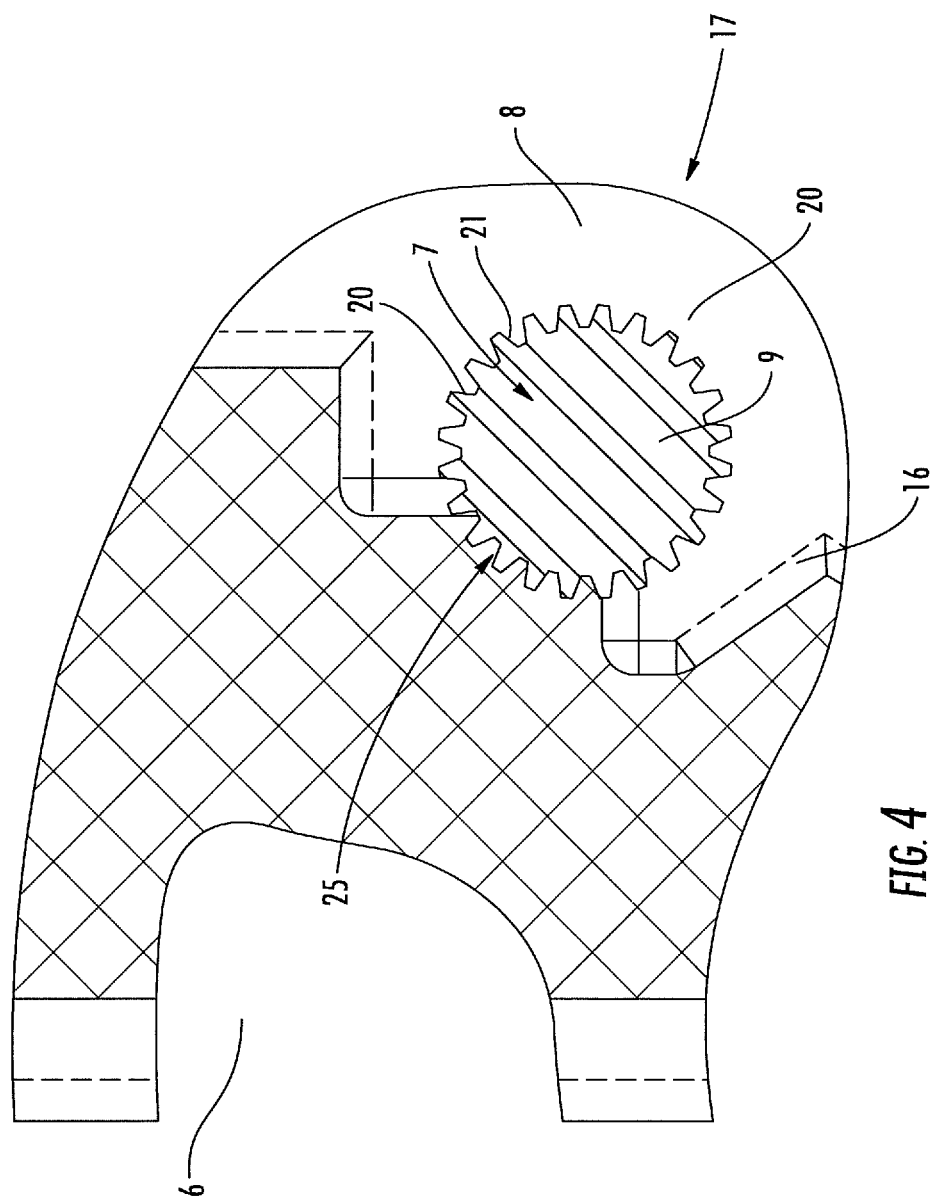
FIG. 4 is a partial cross-sectional view of a side portion of the implant of FIG. 1 taken along the line A-A.
Figure 7:
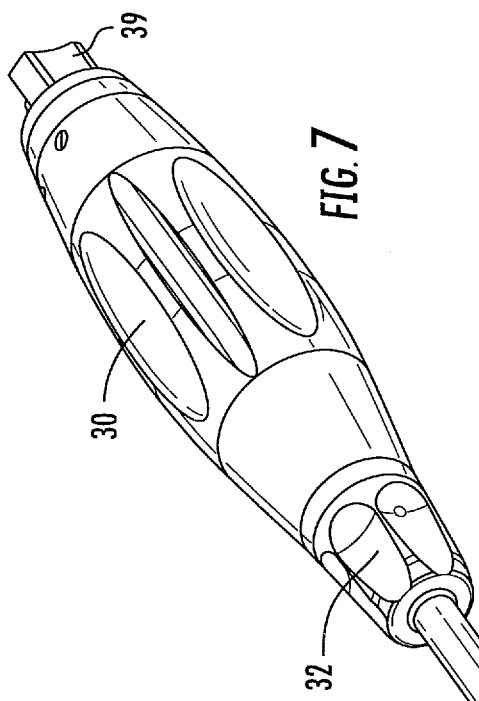
FIG. 7 is a perspective view of the instrument of FIG. 5.

A portion 25 of the splined shaft 9 is embedded in the body 2 with a main portion that is on the contrary accessible through the opening 8, as clearly shown in the cross section of FIG. 4. This accessible or exposed portion 25 may involve an opening between 180° to 320°.

This portion 25 may be specifically provided in an injection mold when the implant body 2 and the splined shaft 9 are realized by different materials; otherwise, the portion 25 is simply integrally formed with the implant body 2 as a single piece construction. Advantageously, the splined shaft 9 has a substantially cylindrical shape presenting a plurality of ribs 20 along its peripheral surface. Those ribs 20 are regularly angularly spaced by grooves 21 as in a gear and provided in a number varying from ten to eighty.

More particularly, the splined shaft 9 has a plurality of ribs 20 regularly alternated by groves 21 with a regular and relatively small pitch, thus forming the gear shape of the shaft. This particular shape allows the embedded portion 25 to be strongly gripped by the implant body 2 so that there is a strong mechanical integration and fixation between the implant body 2 and the splined shaft 9 if they are made with different materials. In embodiments where the implant body and the splined shaft are formed by a single piece construction, it should be noted that the accessible portion 25 of the splined shaft 9 would present a partially cylindrical projection of alternated ribs 20 and grooves 21.

The implant 1 may be clamped by the gripping end of the instrument 12 through the splined shaft 9 but this clamping action may be performed in different positions of the accessible portion 25, as seen hereinafter. The splined shaft 9 offers a positive lock between the grasping head 10 of the instrument 12 and the implant 1.

The opening 8 is delimited by at least a lateral wall 16 that represents a lateral stop for the possible angular orientation of the grasping head 10 of the instrument 12 when such a grasping head 10 is engaging the splined shaft 9. This mechanical stop 16 gives a feedback of the position of the implant 1 in relation to the positioning or insertion instrument 12. The splined shaft 9 allows fixing the grasping head 10 of the instrument 12 in multiple predefined positions in respect to the implant 1. Moreover, the interface allows for transferring a maximal amount of torque, as well as a high axial force, between the instrument and the implant.

As previously mentioned, the material for realizing the implant body 2 may be the same as the material for realizing the splined shaft 9. As an alternative, the two materials may be advantageously different. For example, and without limiting the present disclosure, the body 2 of the implant 1 may be manufactured by PEEK while the splined shaft 9 may be manufactured by a suitable biocompatible alloy, for example, Titanium or a Titanium alloy. Such a combination of materials renders the instrument/implant interface strength greater in tension as well as in torsion compared to a possible pure PEEK interface.

Moreover, the presence of the metal splined shaft 9 allows employing only a couple of markers 18 located preferably on the opposite side of the implant 1 with respect to opening 8, that is to say close to the insertion nose 15. This is because the shape of the splined shaft 9 allows for easy identification of the position of the implant 1 in combination with just a couple of markers 18 located, for example, in the opposite side. The splined shaft 9 offers a rigid interface as well as a higher freedom to handling if compared to the typical interface systems and allows transferring the torque needed to turn the implant in situ.

The implant of the present disclosure has many advantages; for example, it has a very simple and low cost construction that may be easily and firmly handled by the instrument for inserting or removing the implant into and out from an intervertebral space between adjacent vertebral bones. Thanks to the implant structure, the instrument needs much less space for in-situ manipulation than the typical handling and locking mechanisms. Space may be critical due to the fact that it drives up the size of the surgical incision. This function enables minimally invasive implantation as the implant can be inserted in the direction of the smallest cross section and the turned in situ into the correct position. Moreover, due to the stable lock between the instrument and the implant, a perfect controlled angular adjustability of the implant in-situ is possible.

Referring now to the examples of FIGS. 5 to 19, it is disclosed hereinafter in detail the positioning instrument 12 used for handling the above-described implant 1. The present disclosure also relates to the instrument 12 structured for positioning an intervertebral implant like the implant 1 in the spinal column. The instrument 12 allows for simple grasping of the implant 1 by the instrument grasping head and with a quick 90° oval locking feature.

The connection is allowed by way of the ribs and grooves of the splined shaft 9 in the implant 1 and the corresponding teeth of clamps 45, 46 forming the grasping head 10 that allows the fixation at one predefined position or the fixation in multiple predefined positions to the instrument. The connection is allowed by way of the ribs and grooves of the splined shaft 9 in the implant 1 and the corresponding teeth of clamps 45, 46, forming the grasping head 10 that allows the fixation at one predefined position or the fixation in multiple predefined positions to the instrument. A simple 90° rotation of the instrument thumb wheel provides a locking mechanism that significantly simplifies the engagement and disengagement of the implant 1 or of a similar implant structure, as seen hereinafter.

In addition, typical instruments with a significant axial displacement can cause tissue damage. Pliers-like instruments usually have an excessive space requirement, which is in certain applications critical because it may require larger incisions and can usually not be used in Minimal Invasive surgeries. The positioning instrument 12 for the TLIF implant comprises various components.

A handle 30 allows secure holding of the instrument 12. Inside the handle, an elongated sleeve 31 is hosted. The distal end 33 of this sleeve 31 is connected to a locking shaft 35 that is extended along an X axis aligned with the same axis of the handle 30. The locking shaft 35 terminates with a distal end portion including the grasping head 10.

A collar 44 is mounted on the distal end of the locking shaft 35 while the grasping head 10 extends outside the collar 44. The locking shaft 35 is longer than the handle 30, and the connection between the shaft 35 and the distal end of the sleeve 31 is protected by a thumb wheel 32. The connection between the thumb wheel 32 and the distal end 33 of the sleeve 31 may be obtained in different manner, but a bayonet coupling 34 is preferred in this embodiment, as shown in FIG. 14.

Figure 15:
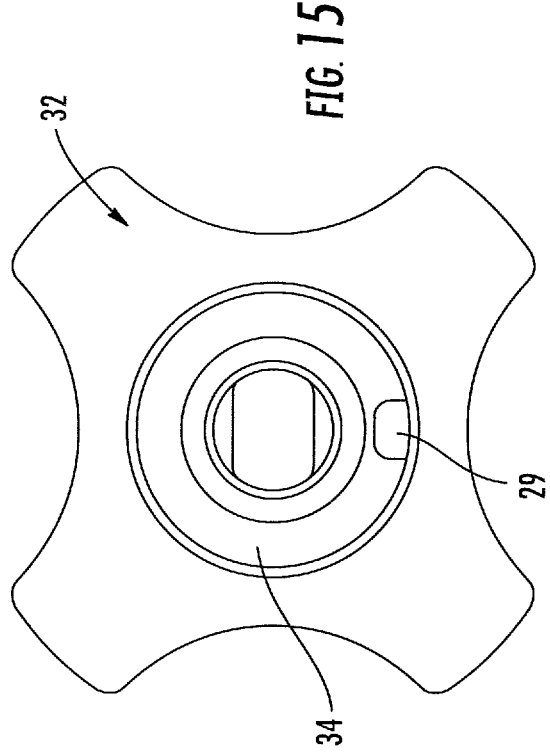
FIG. 15 is a front view of a particular of the instrument, according to the present invention.
Figure 16:
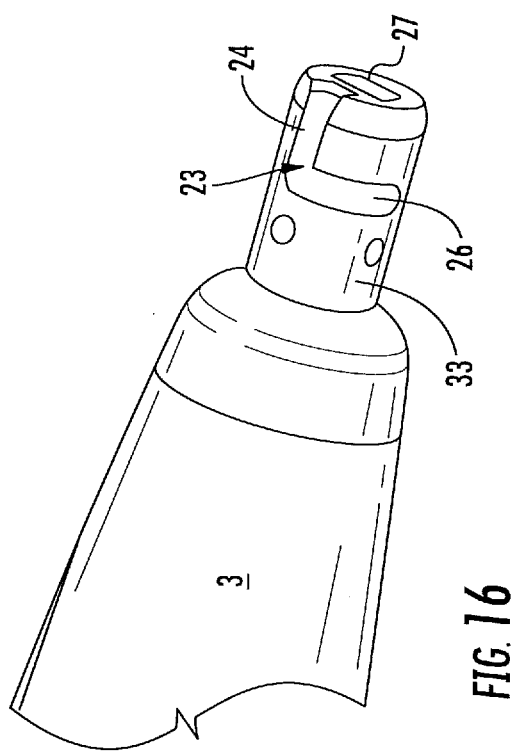
FIG. 16 is a perspective view of another particular of the instrument, according to the present invention.
Figure 19:
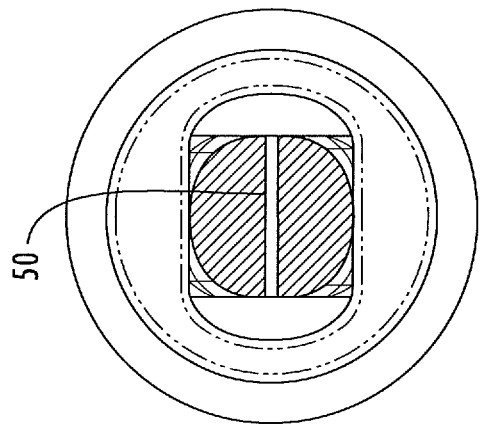
FIGS. 17, 18, and 19 are cross-sectional views of the instrument distal portion taken along the line F-F of FIG. 6 in different operative conditions, respectively.

In more detail, as shown in FIGS. 15 and 16, the distal end 33 of the sleeve 31 includes a groove 23 having an L shape. A first portion 24 of this groove is elongated parallel to the axis X-X of the shaft 35, while a second portion 26 of this groove 23 is extended perpendicularly to the first groove portion 24 and for a predetermined angular extension that may vary from 10° to 130° according to the application needs.

A pin 29 is projected inside a cavity 34 of the thumb wheel 32. This pin 29 is inserted into the first groove portion 24 when the thumb wheel 32 is mounted on the distal end 33 of the sleeve 31. Then, the pin 29 is trapped into the second groove portion 26 of the L shaped groove 23 to allow an angular excursion of the thumb wheel 32 according to the length of the angular excursion of second groove portion 26.

The locking shaft 35 is cannulated and a stem 38 is inserted inside the shaft 35 and the sleeve 31 up to the proximal end of the handle 30. The longitudinal hole forming the cannulated passage has an oval section only in correspondence of the tip or distal end, i.e. in correspondence of the collar 44, as can be appreciated from the cross section of FIG. 10.

The remaining portion of the shaft 35 is cylindrical, as can be appreciated from the perspective view of FIGS. 13 and 14, showing also the oval section 27 of the sleeve passage. As an alternative, the cannulated passage may have a rectangular section with rounded edges. The stem 38 has a main cylindrical cross section.

The proximal end of this stem 38 is provided with a thread portion 37 to allow the fastening of a terminal fastener nut 39, shown in FIG. 6. The nut 39 prevents the instrument from being disassembled when in use.

The stem 38 and the handle 30 have a partially rectangular cross-section at their interface at the distal end of the handle. This means that the stem 38 cannot rotate with respect to the handle 30. In this embodiment, it is only possible to rotate the locking shaft 35 with respect to the stem 38 and the handle 30 through the thumb wheel 32. However, it's possible to rotate the stem during the assembly phase in order to find the rectangular counter part in the handle 30. Another alternative embodiment may be provided with the locking shaft fixed to the handle and the stem being free to rotate with respect to the locking shaft to cause the locking function. This possible alternative embodiment may be less easy to handle, but nothing prevents adoption of this embodiment in line with the principles of the present disclosure.

In the present embodiment, the cannulated shaft 35 is rotatable on the stem 38. A ball positioner 43 prevents the fastener nut 39 from falling out of the handle 30.

Figure 8:
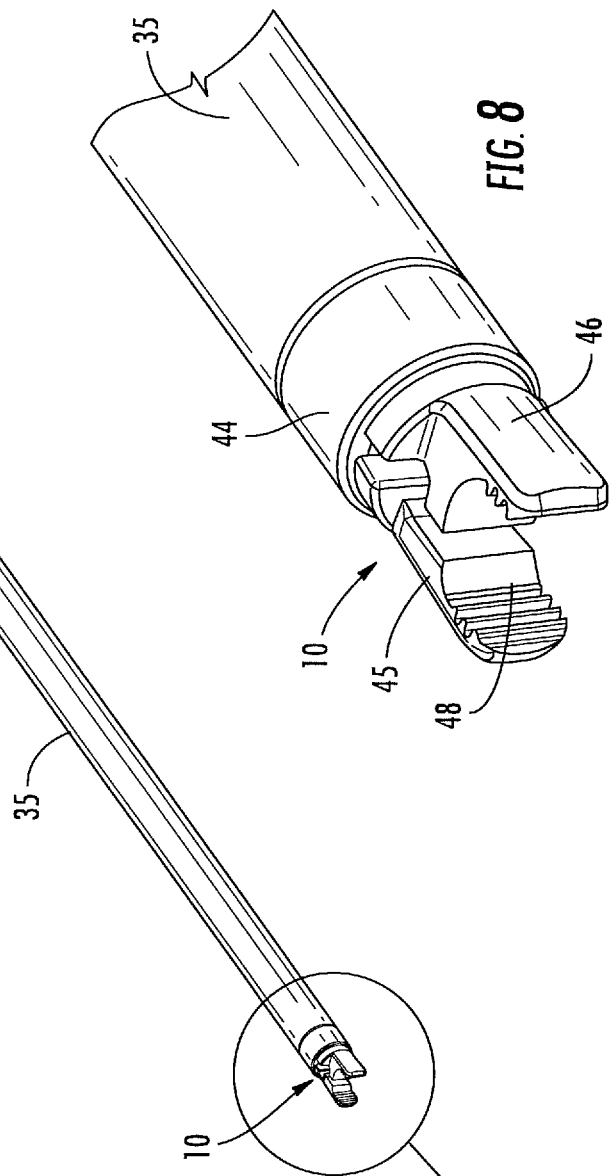
FIG. 8 is a perspective view of a distal portion of the instrument shown in FIGS. 5 and 7.
Figure 9:
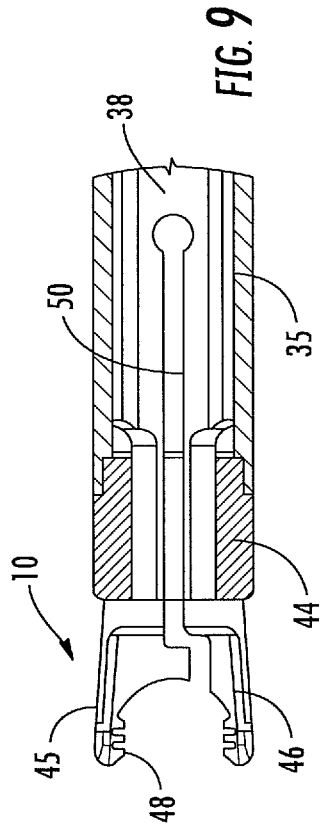
FIG. 9 is a cross-sectional view of the distal portion of FIG. 8.
Figure 10:
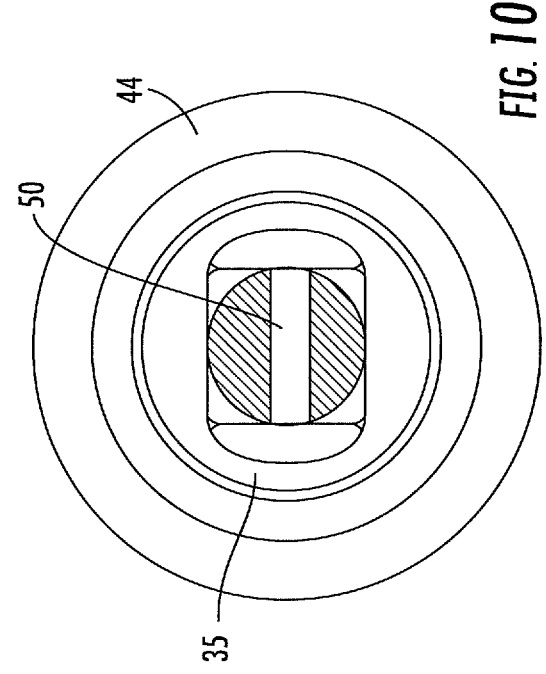
FIG. 10 is a cross-sectional view of the instrument distal portion taken along the line F-F of FIG. 6.

Referring to the examples of FIGS. 8 and 9, the structure of the distal end portion of the instrument 12 will be described. The grasping head 10 is the distal terminal portion of the stem 38 and is formed by a couple of faced clamps 45, 46. Both clamps present an internally curved surface having a teethed portion 48 with ribs and grooves substantially corresponding in shape to the ribs 20 and grooves 21 of the splined shaft 9.

A cut 50 is provided at the distal end of the stem 38 for a short extension, thus separating the two clamps 45, 46 and allowing a reciprocal elastic movement between them. The cut 50 is extended more than the extension of the shaft distal oval section. It should be also noted that the two clamps 45, 46 have a slightly different structure and they are asymmetrical to avoid the presence of a possible groove due to an alignment with the cut 50. This allows for always trapping the splined shaft 9 of the implant 1 in a regular position.

Figure 11:
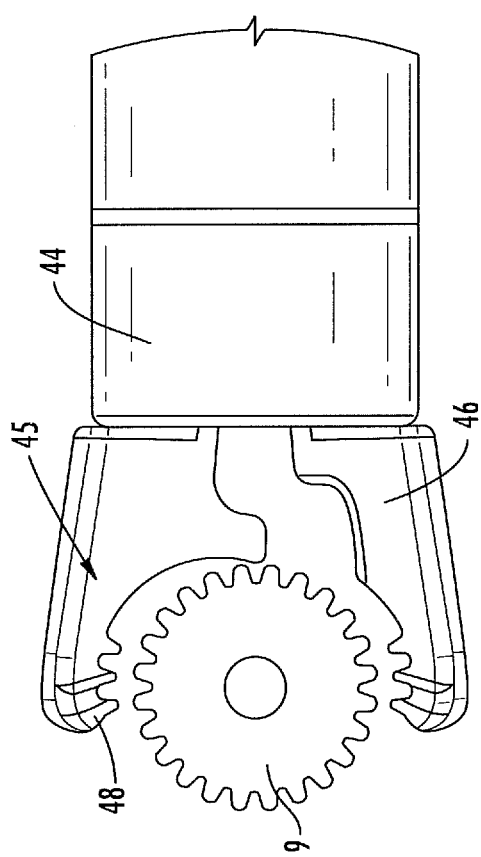
FIGS. 11 and 12 are side views of the instrument distal portion, according to the present invention, in two different operative conditions, respectively.
Figure 12:
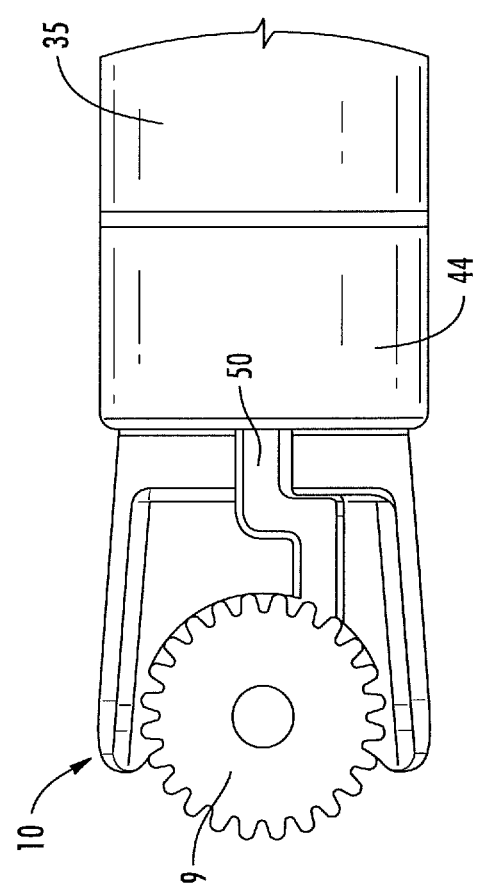

FIGS. 11 and 12 show the grasping head 10 of the positioning instrument 12 in two different operating position, the first approaching the splined shaft 9 of the implant 1 and the second gripping such a splined shaft 9 with the clamps 45, 46 closed on the gear shape of the splined shaft 9. The different relative positions of the stem 38 inside the cannulated locking shaft 35 having internal oval section are shown in the FIGS. 17, 18 and 19.

Figure 18:
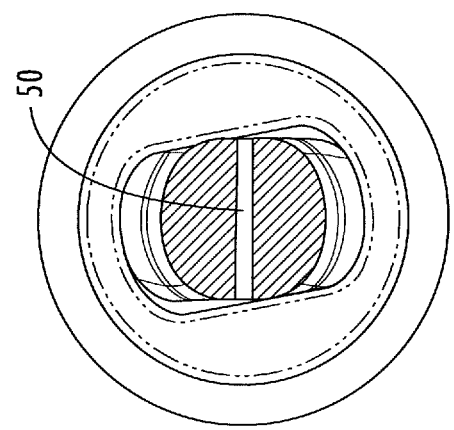
Figure 17:
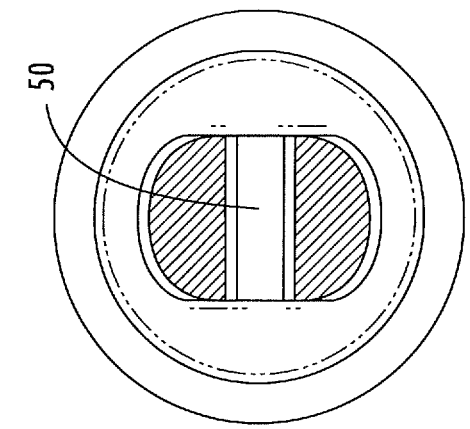

In FIG. 17, the cut 50 shows that the two clamps 45, 46 are in the rest position spaced from the other. In FIGS. 17 and 18, the air gap in the cut 50 is reduced since two end portions of the stem 38 are closer one to the other in view of the rotation of the shaft 35 in one or in the other +/−90° angular position. However, just a reduced angular movement of only 10° may start the approaching movement of the two end portion of the stem forming the clamps 45, 46.

The rotational movement to lock the grasping head 10 can be between 10° and 130° degree. A 90° degree movement is a preferred locking option; however, the instrument structure may allow a free relative rotation between the shaft 35 and the stem 38 between 0° and 130° with continuity. It should be noted that all essential parts of the instrument 12 can be disassembled for cleaning and sterilization.

The instrument locking function is operated with the help of the thumb wheel 32, which is part of the locking shaft 35. By turning the thumb wheel for +/−90° a relative movement with respect to the stem 38 is obtained for the cannulated shaft 35. An angular excursion between 10° and 90° may allow performance of a gripping action of the two clamps 45, 46. The core element of the instrument 12 is the stem 38, which can be secured inside the handle 30 with the help of the fastener nut 39 screwed on the threaded portion 37 of the stem proximal end but it is supporting a rotatable shaft 35.

The locking shaft 35 is secured along the axial direction on the instrument 12 with the help of a fast bayonet coupling 33. The grasping head 10 of the stem 38 in its rest position is normally pre-deformed in order to offer an open position of the instrument 12 ready to grip the splined shaft 9 of the implant 1. The shaft 35 can be turned or rotated over the stem 38 covering +/−90°, and the oval section of the cannulated shaft 35 allows performance of an equal turning movement. This rotation results in a closing movement of the two clamps 45, 46 of the grasping head 10 that approaches one close to the other gripping the splined shaft 9 of the implant 1, as shown in FIGS. 13 and 14.

The internal oval section of the locking shaft 35 forces the two distal portions of the stem 38 forming the grasping head 10, and separated by the cut 50, into a locking position as shown in the FIG. 12. This function is used to grab or release the splined shaft 9 of the implant 1 and allows holding/manipulating the implant at several angles. When locking, the ribs 20 are engaged and allow the transmission of torque in order to manipulate and correctly positioning the implant in situ. When an angle between the implant and the instrument of at least of 60° is reached, the mechanical stop 16 avoids further increase of the angle as it is in contact with the stopping surface of the instrument clamps 45 or 46. This gives feedback of the position of the implant relative to the instrument.

That which is claimed is:

1. An intervertebral implant for fusion between first and second vertebral bodies of a vertebral column, the intervertebral implant comprising:
   a body having opposing first and second ends, opposing first and second sides, and opposing first and second surfaces extending between the opposing first and second ends and between the opposing first and second sides, said body defining a cavity in the first end thereof; and a splined shaft extending between the opposing first and second surfaces, being accessible through the cavity, and having a plurality of peripheral ribs regularly angularly spaced by a plurality of grooves to define a geared interface for receiving an instrument;

said opposing first and second surfaces each comprising a geared opening for receiving the geared interface of said splined shaft so that said splined shaft is rotationally fixed with respect to said body;

a radial portion of said splined shaft being embedded in said body adjacent said cavity and along an entire length of said splined shaft.

2. The intervertebral implant according to claim 1, wherein said body comprises a biocompatible radiolucent synthetic material; and wherein said splined shaft comprises one of a biocompatible metal or a metal alloy.

3. The intervertebral implant according to claim 1, wherein said splined shaft is substantially perpendicular to said opposing first and second surfaces.

4. The intervertebral implant according to claim 1, wherein said cavity has an angular range between 180 to 320 degrees; and wherein the first end comprises at least one lateral wall to define a stop for the instrument.

5. The intervertebral implant according to claim 1, wherein the second end defines an insertion nose opposite said splined shaft.

6. The intervertebral implant according to claim 1, further comprising a plurality of markers carried by said second end.

7. The intervertebral implant according to claim 1 wherein each of the first and second surfaces comprises a plurality of teeth to engage a respective vertebral body.

8. The intervertebral implant according to claim 7 wherein said splined shaft includes first and second ends respectively defining portions of the opposing first and second surfaces, such that the plurality of teeth form a regularly distributed teethed interface across the first surface and the first end of the splined shaft and across the second surface and the second end of the splined shaft.

9. The intervertebral implant according to claim 1 wherein said body defines a plurality of additional cavities formed through and distributed among the opposing first and second sides and surfaces.

10. The intervertebral implant according to claim 1 wherein the second end has tapered portions.

11. A method for making an intervertebral implant for fusion between first and second vertebral bodies of a vertebral column, the method comprising:

injection molding a body having opposing first and second ends, opposing first and second sides, and opposing first and second surfaces extending between the opposing first and second ends and between the opposing first and second sides, the body defining a cavity in the first end thereof; and coupling a splined shaft to extend between the opposing first and second surfaces, be accessible through the cavity, and have a plurality of peripheral ribs regularly angularly spaced by a plurality of grooves to define a geared interface for receiving an instrument, the opposing first and second surfaces each comprising a geared opening for receiving the geared interface of the splined shaft so that the splined shaft is rotationally fixed with respect to the body;

a radial portion of the splined shaft being embedded in the body adjacent the cavity and along an entire length of the splined shaft.

12. The method according to claim 11 wherein each of the first and second surfaces comprises a plurality of teeth to engage a respective vertebral body.

13. The method according to claim 12 wherein the splined shaft includes first and second ends respectively defining portions of the opposing first and second surfaces, such that the plurality of teeth form a regularly distributed teethed interface across the first surface and the first end of the splined shaft and across the second surface and the second end of the splined shaft.

14. The method according to claim 11 wherein the body defines a plurality of additional cavities formed through and distributed among the opposing first and second sides and surfaces.

15. The method according to claim 11 wherein the second end has tapered portions.

16. The method according to claim 11 further comprising forming a plurality of markers carried by the second end.

* * * * *